US00PP37226P2

(12) United States Plant Patent
Gómez Porras et al.

(10) Patent No.: US PP37,226 P2
(45) Date of Patent: Jan. 27, 2026

(54) OLIVE TREE NAMED 'I-51'

(50) Latin Name: *Olea europaea*
Varietal Denomination: I-51

(71) Applicant: TODOLIVO S.L., Cordova (ES)

(72) Inventors: José María Gómez Porras, Cordova (ES); Diego Barranco Navero, Cordova (ES); Luís Rallo Romero, Cordova (ES); Concepción Muñoz Díez, Cordova (ES); Carlos Trapero Ramírez, Cordova (ES); Pedro Valverde Caballero, Cordova (ES)

(73) Assignee: TODOLIVO S.L., Cordova (ES)

( * ) Notice: Subject to any disclaimer, the term of this patent is extended or adjusted under 35 U.S.C. 154(b) by 0 days.

(21) Appl. No.: 19/086,806

(22) Filed: Mar. 21, 2025

(51) Int. Cl.
*A01H 6/00* (2018.01)
*A01H 5/08* (2018.01)

(52) U.S. Cl.
USPC ..... Plt./158

(58) Field of Classification Search
USPC ..... Plt./158
CPC ..... A01H 6/00; A01H 5/08
See application file for complete search history.

*Primary Examiner* — Keith O. Robinson
(74) *Attorney, Agent, or Firm* — Hunt IP Law

(57) ABSTRACT

The new and distinct variety of olive tree variety 'I-51' is provided. The variety can be distinguished by its outstanding features of drooping growth habit, high yield, and high oil content.

5 Drawing Sheets

CROSS REFERENCE TO RELATED APPLICATIONS

Co-pending U.S. application Ser. No. 18/445,927 filed Mar. 27, 2024, Ser. No. 18/445,919 filed Mar. 27, 2024, Ser. No. 18/445,920 filed Mar. 27, 2024, Ser. No. 18/445,930 filed Mar. 27, 2024, Ser. No. 18/445,926 filed Mar. 27, 2024, Ser. No. 18/445,922 filed Mar. 27, 2023, Ser. No. 18/445,921 filed Mar. 27, 2024, Ser. No. 18/445,924 filed Mar. 27, 2024, Ser. No. 18/445,929 filed Mar. 27, 2024; disclose olive tree varieties named 'I 24', 'I 72', 'I 74', 'I 77', 'I 46', 'I 79', 'I 99', 'I 100', and 'I 101' respectively. Such applications are related inasmuch as they have the same parentage, ownership, and/or inventorship.

Latin name of the genus and species:

Botanical classification: a. Genus—*Olea*. b. Species—*europaea*.

Variety denomination: The new olive tree claimed is of the variety denominated 'I-51'.

BACKGROUND OF THE INVENTION

Field of the Invention

The present invention relates to a new and distinct variety of olive tree, which has been given the variety denomination of 'I-51'.

Background of the Related Art

Olive oil continues to increase in popularity. Accordingly, there is a continuing need to develop new and improved olive oils to meet the increased demand for use in various food types and for its well-known antioxidant function and healthy effect. Many olive varieties are self-sterile. Currently, olive growing is in a process of change and there is a great need to develop new varieties that adapt to the new hedgerow cultivation systems, the system most used in plantations today. Very few varieties adapt to this system, so the development of new varieties that expand the current range with agronomic differences or differences in the composition of their oils is of vital importance.

SUMMARY OF THE INVENTION

The present invention relates to a new and distinct variety of olive tree, which has been given the variety denomination of 'I-51'. 'I-51' is intended for use for olive oil production.

The new olive tree variety is a selection resulting from a controlled sexual cross of olive trees at Córdoba, Spain in 2008, involving a pollen parent known as 'Arbosana' (unpatented) and a seed parent known as 'Koroneiki' (unpatented).

The selection was subsequently evaluated for 10 years at Córdoba, Spain.

Asexual reproduction of the new variety by cutting propagation since 2014 at Córdoba, Spain has demonstrated that the new variety reproduces true to type with all of the morphological characteristics, as herein described, firmly fixed and retained through successive generations of such asexual propagation.

Selection criteria were early production, spreading growth habit, high yield, and high oil content.

This new variety stands out for its high production. Compared to its parents, produces 5-15% more than 'Koroneiki' and a similar production than 'Arbosana'. The vigor of 'I-51' is similar to that of 'Arbosana' and is less vigorous than 'Koroneiki'. The growth habit of 'I-51' is drooping while that of 'Arbosana' is spreading.

Plants of the new variety differ from the varieties mentioned in co-pending application Ser. No. 18/445,926 (for Olive Tree Named 'I 46'), Ser. No. 18/445,927 (for Olive Tree Named 'I 24'), Ser. No. 18/445,919 (for Olive Tree Named 'I 72'), Ser. No. 18/445,920 (for Olive Tree Named 'I 74'), Ser. No. 18/445,930 (for Olive Tree Named 'I 77'), Ser. No. 18/445,921 (for Olive Tree Named 'I 99'), Ser. No.

18/445,924 (for Olive Tree Named 'I 100'), and Ser. No. 18/445,929 (for Olive Tree Named 'I 101') as shown in Table 1 below:

TABLE 1

| Variety Denomination | Parentage | Growth Habit | Vigor | Outstanding Agronomic Characteristics |
|---|---|---|---|---|
| 'I 46' | 'Arbosana' x 'Koroneiki' | Open | Medium | Extra-early ripening, high fat yield. |
| 'I 24' | 'Arbosana' x 'Koroneiki' | Weeping | Low | High production, good fat yield, drought tolerant |
| 'I 72' | 'Arbosana' x 'Koroneiki' | Upright | Medium | High production, drought tolerant |
| 'I 74' | 'Arbosana' x 'Koroneiki' | Open-Straight | Medium | Good production, drought tolerant |
| 'I 77' | 'Koroneiki' x 'Arbosana' | Compact | Medium-low | Good production, high fat yields |
| 'I 79' | 'Koroneiki' x 'Arbosana' | Open | Medium-high | High fat yields |
| 'I 99' | 'Arbosana' x 'Chiquitita' | Weeping | Low | High fat yield, drought tolerant |
| 'I 100' | 'Arbosana' x 'Chiquitita' | Weeping and Upright | Low | Drought tolerant |
| 'I 101' | 'Arbosana' x 'Chiquitita' | Weeping and Upright | Low-medium | Good fat yield, drought tolerant |

BRIEF DESCRIPTION OF THE DRAWINGS

The accompanying photographic illustrations show the typical appearance of the new variety 'I-51'. The colors are as nearly true as is reasonably possible in a color representation of this type. Colors in the photographs may differ slightly from the color values cited in the detailed botanical description which accurately describes the colors of the new plant. The images that will be illustrated below have been taken on 5-year-old plants, planted in Córdoba, Spain.

DETAILED BOTANICAL DESCRIPTION

Figure 1:
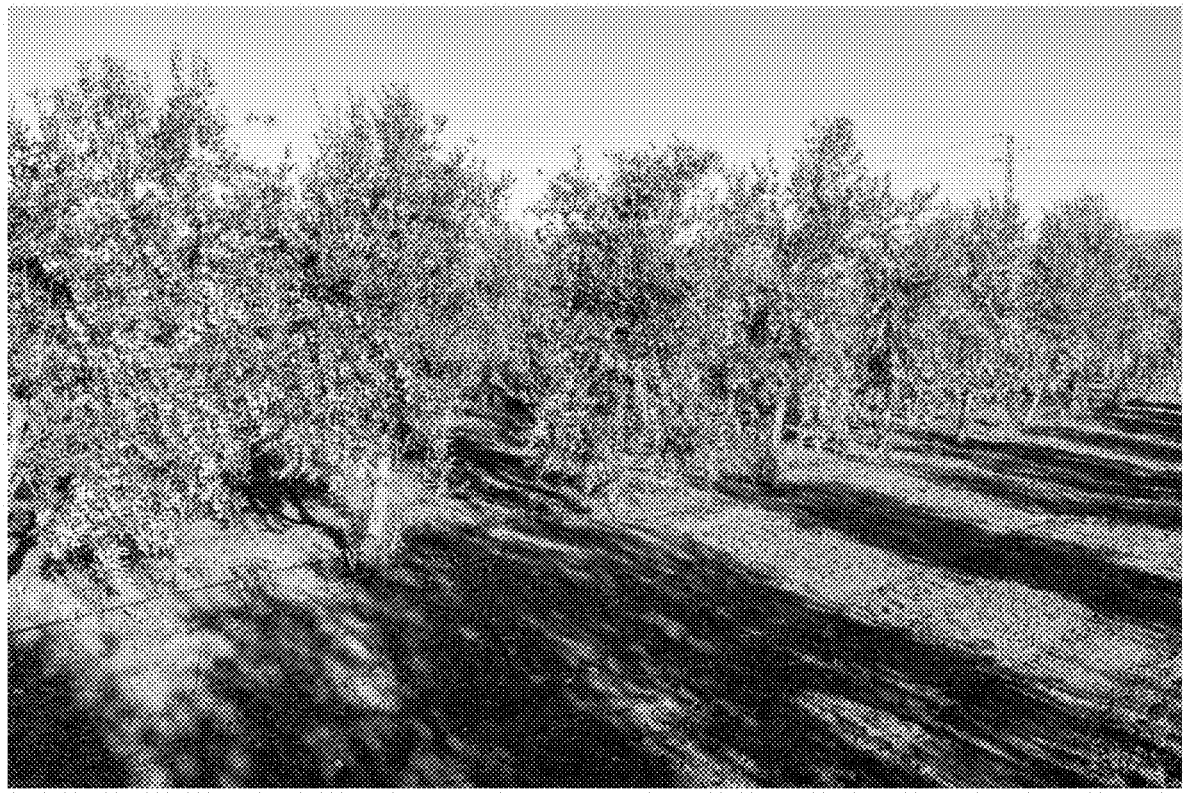
FIG. 1 is a photograph of the new variety 'I-51', demonstrating the behavior of the variety when grown in a hedge line.
Figure 2:
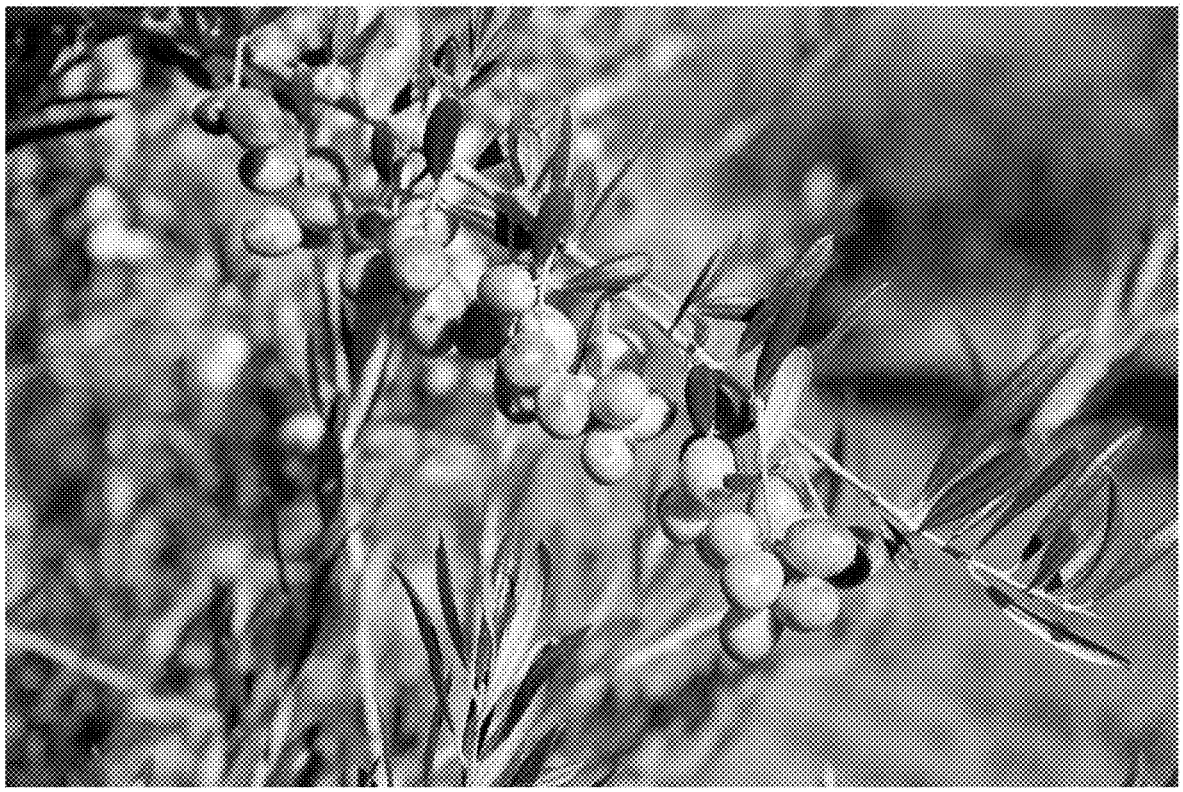
FIG. 2 is a photograph of the new variety 'I-51', demonstrating fruit size and fruit color.
Figure 3:
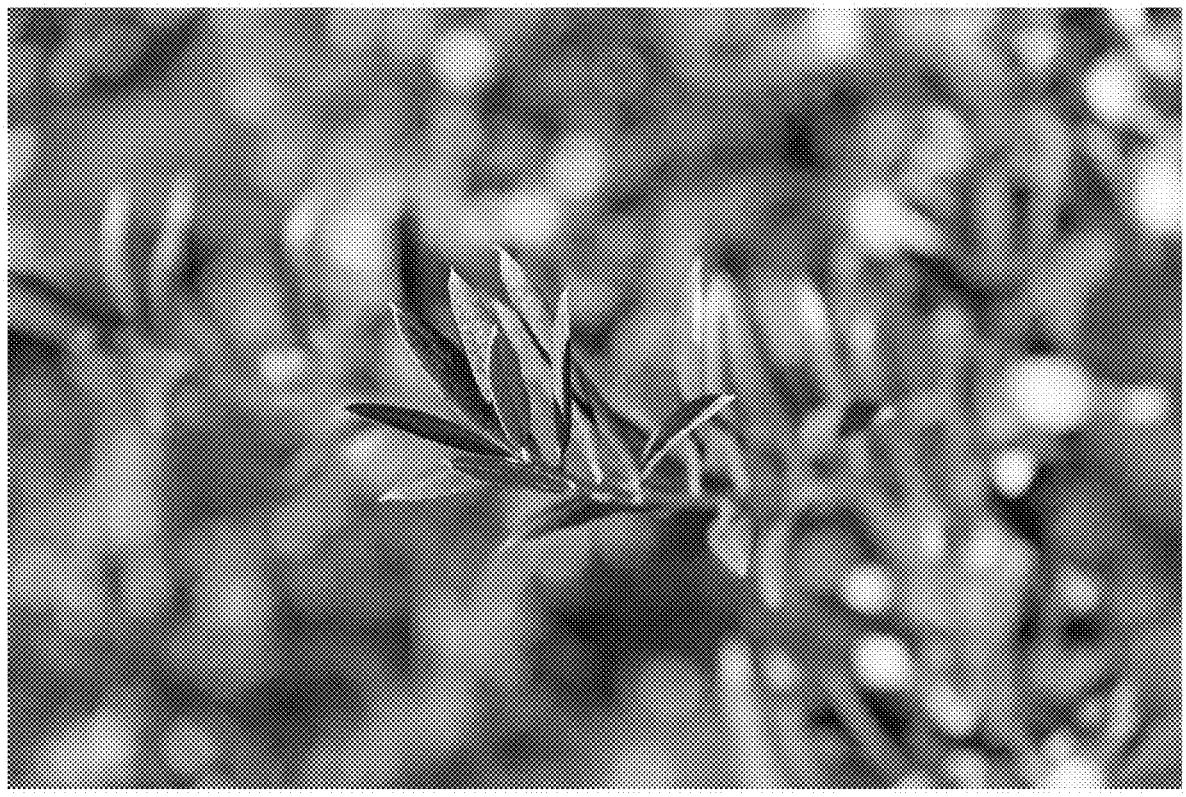
FIG. 3 is a photograph of the new variety 'I-51', demonstrating detail of the leaves of the new variety 'I-51'.
Figure 4:
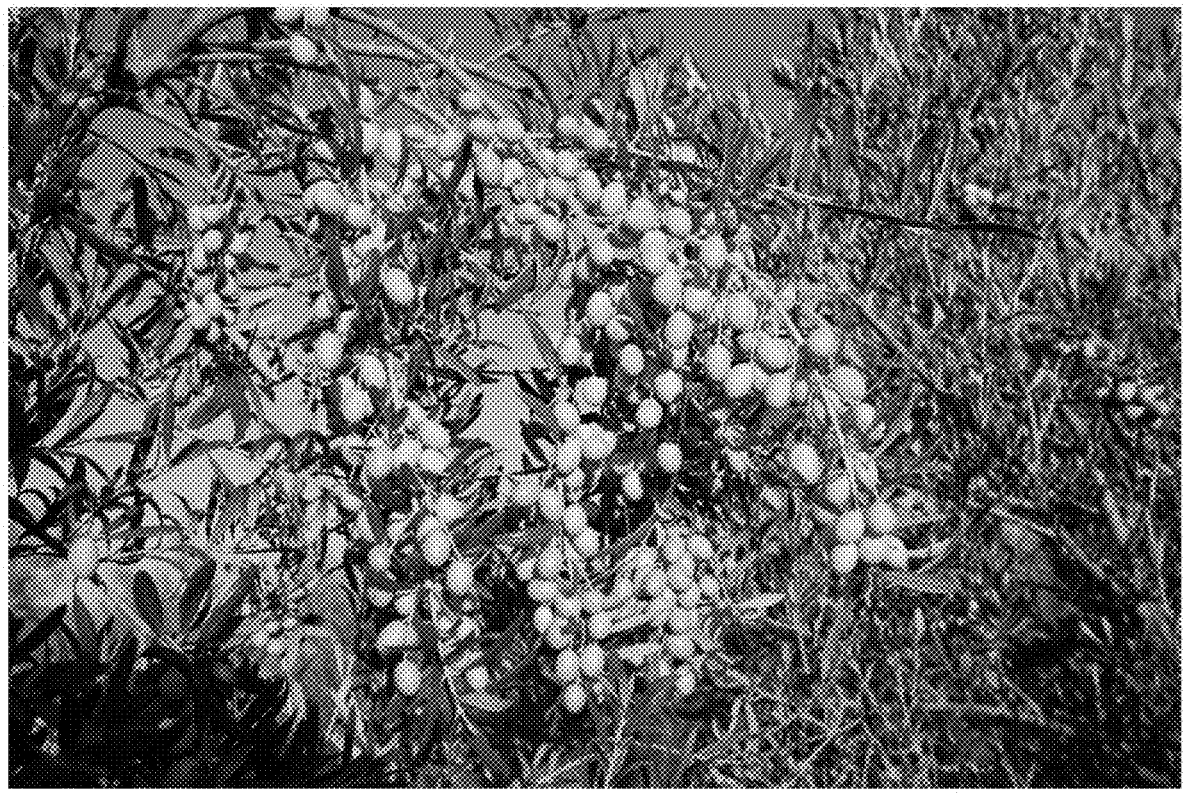
FIG. 4 is a detailed photograph of the new variety 'I-51', demonstrating several productive branches.
Figure 5:
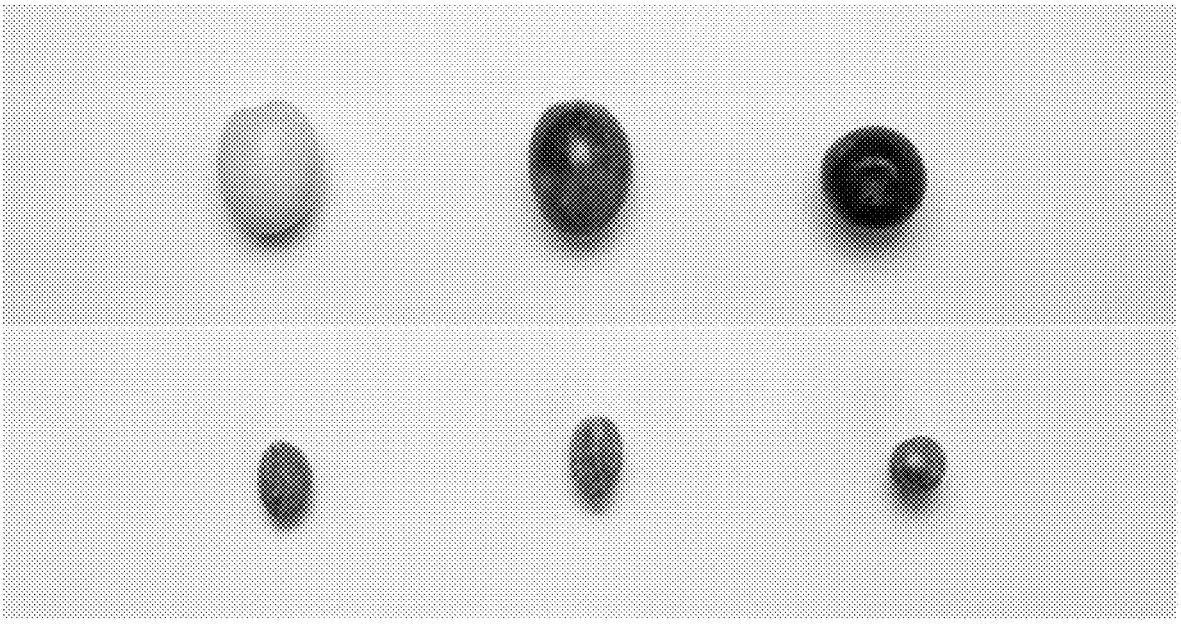
FIG. 5 is a detailed photograph of the new variety 'I-51', demonstrating fruits and stones. Left and center depict the side view. Right depicts stalk end view.

The following detailed description sets forth the distinctive characteristics of 'I-51'. The datum which defines these characteristics was collected from asexual reproductions of the original selection. Dimensions, sizes, colors, and other characteristics are approximations and averages set forth as accurately as possible. The plant history was taken on plants approximately 5 years of age, and the descriptions relate to plants grown in Córdoba, Spain. Color notations are in reference to the standard Color Chart is that of The Royal Horticultural Society (R.H.S. Colour Chart, 2015 edition. London, England).

Classification:

a. *Latin name.*—*Olea europaea* L.
b. *Common name.*—Olive tree.
c. *Variety name.*—'I-51'.

Parentage:

a. *Female parent.*—'Arbosana' (unpatented).
b. *Male parent.*—'Koroneiki' (unpatented).

PLANT

General:

a. *Height.*—212 cm (average).
b. *Width.*—138 cm (average).
c. *Growth habit.*—Drooping.
d. *Vigor.*—Medium.
e. *Canopy density.*—Dense.

ROOTS

General:

f. *Rooting habit.*—Normal-Dense.
g. *Texture.*—Fibrous.
h. *Color designation* (*young roots*).—155A.
i. *Color designation* (*old roots*).—157A.

STEMS

General:

j. *Branching habit.*—Weak.
k. *Trunk.*—i. Circumference — 8 cm. ii. Surface texture — Smooth. iii. Color — 199A.
l. *Main stems.*—i. Quantity — 2-5. ii. Aspect — Upward. iii. Strength — Medium. iv. Cross-section — Rounded. v. Circumference — 5 cm (diameter) at 50 cm. vi. Surface texture (young stems) — Smooth. vii. Surface texture (mature stems) — Smooth with lenticels. viii. Color designation (young stems) — 157A. ix. Color designation (mature stems) — 157B. x. Lenticels — (140 average), 1 mm long 0.5 mm wide. xi. Internode length — Ranging from 5-12 cm.
m. *Lateral branches.*—i. Quantity — 5-8. ii. Cross-section — Oval. iii. Length — 140 cm. iv. Internode length — Ranging from 2-3 cm. v. Texture — Smooth with raised lenticels. vi. Aspect — Outward. vii. Strength — Flexible. viii. Color (young lateral branches) — 196D. ix. Color (mature lateral branches) — 197D. x. Pubescence — None. xi. Diameter — 12 cm.

FOLIAGE

General:

n. *Arrangement.*—Opposite.
o. *Attachment.*—Petiolate.
p. *Division*-Simple.
q. *Lamina.*—i. Length — 48 mm (average). ii. Width — 9 mm (average). iii. Thickness — 1.0-1.5 mm. iv. Shape — Acuminate. v. Aspect — Recurved. vi. Apex — Acuminate. vii. Base — Cuneate. viii. Margin — Entire (smooth). ix. Texture of upper surface — Smooth. x. Texture of lower surface — Slightly pubescent. xi. Color of young lamina (upper surface) — 141B. xii. Color of young lamina (lower surface) — 142B. xiii. Color of mature lamina (upper surface) — 143B. xiv. Color of mature lamina (lower surface) — 142B. xv. Venation pattern — Pinnate.

r. *Petiole*.—i. Length — 1.5-2 mm. ii. Diameter — 1.0 mm. iii. Texture — Smooth. iv. Strength — Medium. v. Color — 142B.

s. *Curvature of longitudinal axis of leaf blade*.—Recurved.

INFLORESCENCE

General:

t. *Type*.—Panicle.

u. *Natural flowering season*.—Spring.

v. *Flowering habit*.—1-10 days during April.

w. *Length*.—2.5-6.5 cm.

x. *Width*.—1-3 cm.

y. *Quantity of florets per inflorescence*.—15-25.

z. *Peduncle*.—i. Length — 2.0-6.0 cm. ii. Width — 1.3 cm. iii. Texture — Smooth. iv. Strength — Medium. v. Color — 141D.

aa. *Pedicels*.—i. Length — 2 mm. ii. Width — 1 mm. iii. Texture — Smooth. iv. Strength — Medium. v. Color — 141D.

FLOWER BUD

General:

bb. *Shape*.—Globular.

cc. *Length*.—2-4 mm.

dd. *Width*.—2 mm.

ee. *Color*.—157A.

FLOWER

General:

ff. *Type*.—Perfect.

gg. *Shape*.—Cruciform.

hh. *Persistence*.—Medium.

ii. *Fragrance*.—Licorice-like floral scent.

jj. Diameter.—4-7 mm.

kk. Height.—3-4 mm.

ll. *Calyx*.—i. Quantity of sepals — 4. ii. Arrangement — Rotate. iii. Diameter — 1 cm.

mm. *Sepals*.—i. Sepal fusion — Fused. ii. Length — 1 mm. iii. Width — 1 mm. iv. Shape — Bell shape. v. Apex — Obtuse. vi. Base — Cuneate. vii. Margin — Entire. viii. Texture — Uniform, exhibiting a smooth texture on both the upper and lower surfaces. ix. Color (upper surface) — 149A. x. Color (lower surface) — 149A.

nn. *Petals*.—i. Arrangement — Rotate. ii. Quantity — 4. iii. Fusion — Sympetalous petals fused at the proximal half of the corolla. iv. Shape — Acute. v. Apex — Acute. vi. Base — Cuneate. vii. Margin — Entire. viii. Texture — Uniform, exhibiting a smooth texture on both the upper and lower surface. ix. Color when opening (upper surface) — NN155D. x. Color when opening (lower surface) — NN155D. xi. Color when fully opened (upper surface) — NN155D. xii. Color when fully opened (lower surface) — NN155D. xiii. Color fading — None.

REPRODUCTIVE ORGANS

General:

oo. *Androecium*.—i. Stamen quantity — 2. ii. Filament length — Approximately 0.75 mm. iii. Filament color — 130B. iv. Anther attachment — Basifixed. v. Anther shape — Hemispherical. vi. Anther size (length) — 1 mm. vii. Anther color — 2A. viii. Abundance of pollen — Abundant. ix. Pollen color — 2A.

pp. *Gynoecium*.—i. Pistil quantity — 1. ii. Stigma shape — Bifid cone shape. iii. Stigma length — Approximately 0.75 mm. iv. Stigma color — 145D. v. Style length — Approximately 0.75 mm. vi. Style color — 145D. vii. Ovary position — Superior. viii. Ovary shape — Round. ix. Ovary diameter — Approximately 0.75 mm. x. Ovary color — 145D.

SEED AND FRUIT

General:

qq. *Fruit*.—i. Date of maturity — November. ii. Size — Medium. iii. Weight — 1.8 g. iv. Diameter — 15 mm. v. Length — 19 mm. vi. Form — Elongated. vii. Suture — None. viii. Stem cavity — Medium. ix. Stem length — 5 mm. x. Caliper length — 1.5-2 cm. xi. Apex — Acute. xii. Pistil point — No present. xiii. Skin thickness — Less than 1 mm. xiv. Skin texture — Smooth. xv. Skin tendency to crack — None. xvi. Skin color — N92A. xvii. Flesh color — 158C. xviii. Pit color — 144C. xix. Oil/juice production — Extra Virgin Olive Oil. xx. Flavor — Not applicable. xxi. Ripening — Medium. xxii. Fruit nipple — Absent or weak.

tt. *Stone*.—i. Quantity — 1. ii. Shape — Ovate. iii. Type — Slightly asymmetric. iv. Fibers — None. v. Weight — 0.38 g. vi. Length — 15 mm. vii. Width — 7 mm. viii. Thickness — 2 mm. ix. Apex — Rounded. x. Base — Acute. xi. Color — 162B. xii. Texture — Slightly grooved. xiii. Mucron — Present. xiv. Suture — Present. xv. Sides — Round. xvi. Ridges — Absent. xvii. Tendency to split — None.

DEVELOPMENT

General:

a. *Flowering season*.—1-10 days during April.

b. *Harvesting season*.—Third week of November.

c. *Time to produce a fruit bearing tree*.—2-3 years.

d. *Chilling requirements*.—Unknown (in olive in general).

e. *Hardiness*.—Preferably adapted between 30 and 45 degrees on the north and south meridians (general in olive). 2023 USDA Plant Hardiness Zone Map: 8a-11b.

f. *Plant/fruit disease resistance*.—i. Olive leaf spot (*Spilocaea oleaeginea*) — Moderately resistant. ii. *Verticillium* (*Verticillium dahliae*) — Moderately resistant. iii. Tuberculosis (*Pseudomonas savastanoi*) — Moderately resistant.

g. *Fruit market use*.—Extra Virgin Olive Oil.

h. *Fruit yield*.—6-18 kg/tree. 7,000-20,000 kg/ha.

The new variety 'I-51' has not been observed under all possible environmental conditions to date. Accordingly, as occurs in all varieties of olive tree since the varieties do not present the same phenotypic characteristics in all the places where they are grown, it is possible that the phenotypic expression may vary somewhat with changes in light intensity and duration, cultural practices, and other environmental conditions.

What is claimed is:

1. A new and distinct variety of olive tree named 'I-51', as illustrated and described herein.

* * * * *